(12) United States Patent
Hon

(10) Patent No.: US 9,456,632 B2
(45) Date of Patent: *Oct. 4, 2016

(54) ELECTRONIC CIGARETTE

(71) Applicant: Lik Hon, North Point (HK)

(72) Inventor: Lik Hon, North Point (HK)

(73) Assignee: FONTEM HOLDINGS 1 B.V., Amsterdam (NL)

( * ) Notice: Subject to any disclaimer, the term of this patent is extended or adjusted under 35 U.S.C. 154(b) by 254 days.

This patent is subject to a terminal disclaimer.

(21) Appl. No.: 13/740,011

(22) Filed: Jan. 11, 2013

(65) Prior Publication Data
US 2013/0125906 A1 May 23, 2013

Related U.S. Application Data

(60) Continuation of application No. 13/079,937, filed on Apr. 5, 2011, now Pat. No. 8,365,742, which is a division of application No. 12/226,818, filed as application No. PCT/CN2007/001575 on May 15, 2007, now Pat. No. 8,156,944.

(30) Foreign Application Priority Data

May 16, 2006 (CN) .......................... 2006 2 0090805

(51) Int. Cl.
*A24F 47/00* (2006.01)
*H05B 1/02* (2006.01)
(Continued)

(52) U.S. Cl.
CPC ........... *A24F 47/008* (2013.01); *A24F 47/002* (2013.01); *A24F 47/004* (2013.01); *F22B 1/284* (2013.01); *H01M 2/1055* (2013.01); *H01M 10/425* (2013.01); *H01M 10/46* (2013.01); *H02J 7/0042* (2013.01); *H02J 7/0052* (2013.01); *H05B 1/0244* (2013.01);
(Continued)

(58) Field of Classification Search
CPC ............................ A24F 47/008; A24F 47/002
USPC ............................ 131/270, 273; 128/202.21
See application file for complete search history.

(56) References Cited

U.S. PATENT DOCUMENTS 1,775,947 A   9/1930   Robinson
2,057,353 A   10/1936  Whittemore
(Continued)

FOREIGN PATENT DOCUMENTS

CN   2047485 U   11/1989
CN   2084236 U   9/1991
(Continued)

OTHER PUBLICATIONS

European Patent Office, Supplementary European Search Report and Search Opinion for EP 10740882.5, Oct. 16, 2013.
(Continued)

*Primary Examiner* — Michael H Wilson
*Assistant Examiner* — Dionne Walls Mayes
(74) *Attorney, Agent, or Firm* — Perkins Coie LLP

(57) ABSTRACT

An electronic cigarette includes a battery assembly and an atomizer assembly within a housing with the battery assembly electrically connected to the atomizer assembly. The housing has one or more air inlets. A liquid storage component is in contact with a porous component of the atomizer assembly, with the porous component having a run-through hole. A heating wire is in an air flow path through the run-through hole.

19 Claims, 8 Drawing Sheets

(51) Int. Cl.

| | | |
|---|---|---|
| *H05B 3/06* | (2006.01) | |
| *H05B 3/42* | (2006.01) | |
| *F22B 1/28* | (2006.01) | |
| *H01M 2/10* | (2006.01) | |
| *H01M 10/42* | (2006.01) | |
| *H01M 10/46* | (2006.01) | |
| *H02J 7/00* | (2006.01) | |

(52) U.S. Cl.
CPC .............. *H05B 1/0297* (2013.01); *H05B 3/06* (2013.01); *H05B 3/42* (2013.01)

(56) References Cited

U.S. PATENT DOCUMENTS

| | | | |
|---|---|---|---|
| 2,631,219 | A | 3/1953 | Suchy |
| 3,200,819 | A | 8/1965 | Gilbert |
| 3,551,643 | A | 12/1970 | Pricenski et al. |
| 3,934,117 | A | 1/1976 | Schladitz |
| 4,171,000 | A | 10/1979 | Uhle |
| 4,207,457 | A | 6/1980 | Haglund et al. |
| 4,228,925 | A | 10/1980 | Mendelovich |
| 4,641,053 | A | 2/1987 | Takeda |
| 4,735,217 | A | 4/1988 | Gerth et al. |
| 4,756,318 | A | 7/1988 | Clearman et al. |
| 4,771,796 | A | 9/1988 | Myer |
| 4,819,665 | A | 4/1989 | Roberts et al. |
| 4,848,374 | A | 7/1989 | Chard et al. |
| 4,922,901 | A | 5/1990 | Brooks et al. |
| 4,945,929 | A | 8/1990 | Egilmex |
| 4,945,931 | A | 8/1990 | Gori |
| 4,947,875 | A | 8/1990 | Brooks et al. |
| 4,981,522 | A | 1/1991 | Nichols et al. |
| 5,042,470 | A | 8/1991 | Kanesaka |
| 5,060,671 | A | 10/1991 | Counts et al. |
| 5,080,114 | A | 1/1992 | Rudolph et al. |
| 5,095,921 | A | 3/1992 | Losee et al. |
| 5,117,482 | A | 5/1992 | Hauber |
| 5,144,962 | A | 9/1992 | Counts et al. |
| 5,159,940 | A | 11/1992 | Hayward et al. |
| 5,190,060 | A | 3/1993 | Gerding et al. |
| 5,224,498 | A | 7/1993 | Deevi et al. |
| 5,249,586 | A | 10/1993 | Morgan et al. |
| 5,261,424 | A | 11/1993 | Sprinkel, Jr. |
| 5,285,798 | A | 2/1994 | Banerjee et al. |
| 5,322,075 | A | 6/1994 | Deevi et al. |
| 5,388,594 | A | 2/1995 | Counts et al. |
| 5,438,978 | A | 8/1995 | Hardester, III |
| 5,497,791 | A | 3/1996 | Bowen et al. |
| 5,505,214 | A | 4/1996 | Collins et al. |
| 5,591,368 | A | 1/1997 | Fleischhauer et al. |
| 5,666,977 | A | 9/1997 | Higgins et al. |
| 5,666,978 | A | 9/1997 | Counts et al. |
| 5,730,158 | A | 3/1998 | Collins et al. |
| 5,743,251 | A | 4/1998 | Howell et al. |
| 5,746,251 | A | 5/1998 | Bullard |
| 5,799,663 | A | 9/1998 | Gross et al. |
| 5,819,756 | A | 10/1998 | Mielordt |
| 5,878,752 | A | 3/1999 | Adams et al. |
| 5,894,841 | A | 4/1999 | Voges |
| 6,040,560 | A | 3/2000 | Fleischhauer et al. |
| 6,041,789 | A | 3/2000 | Bankert et al. |
| 6,095,153 | A | 8/2000 | Kessler et al. |
| 6,155,268 | A | 12/2000 | Takeuchi |
| 6,164,287 | A | 12/2000 | White |
| 6,178,969 | B1 | 1/2001 | St. Charles |
| 6,196,218 | B1 | 3/2001 | Voges |
| 6,354,293 | B1 | 3/2002 | Madison |
| 6,357,671 | B1 | 3/2002 | Cewers |
| 6,443,146 | B1 | 9/2002 | Voges |
| 6,532,965 | B1 | 3/2003 | Abhulimen et al. |
| 6,557,552 | B1 | 5/2003 | Cox |
| 6,601,776 | B1 | 8/2003 | Oljaca et al. |
| 6,681,998 | B2 | 1/2004 | Sharpe |
| 6,715,494 | B1 | 4/2004 | McCoy |
| 6,772,756 | B2 | 8/2004 | Shayan |
| 6,803,545 | B2 | 10/2004 | Blake et al. |
| 6,810,883 | B2 | 11/2004 | Felter et al. |
| 6,854,461 | B2 | 2/2005 | Nichols et al. |
| 6,854,470 | B1 | 2/2005 | Pu |
| 7,100,618 | B2 | 9/2006 | Dominguez |
| 7,131,599 | B2 | 11/2006 | Katase |
| 7,726,320 | B2 | 6/2010 | Robinson et al. |
| 7,832,410 | B2 | 11/2010 | Hon |
| 7,845,359 | B2 | 12/2010 | Montaser |
| 7,997,280 | B2 | 8/2011 | Rosenthal |
| 8,156,944 | B2 | 4/2012 | Han |
| 2003/0033055 | A1 | 2/2003 | McCrae |
| 2003/0108342 | A1 | 6/2003 | Sherwood et al. |
| 2004/0182403 | A1 | 9/2004 | Andersson et al. |
| 2004/0261802 | A1 | 12/2004 | Griffin |
| 2005/0016550 | A1 | 1/2005 | Katase |
| 2005/0236006 | A1 | 10/2005 | Cowan |
| 2006/0196518 | A1 | 9/2006 | Hon |
| 2008/0276947 | A1 | 11/2008 | Martzel |
| 2009/0095311 | A1 | 4/2009 | Han |
| 2009/0126745 | A1 | 5/2009 | Hon |
| 2009/0151717 | A1 | 6/2009 | Bowen et al. |
| 2009/0188490 | A1 | 7/2009 | Han |
| 2009/0230117 | A1 | 9/2009 | Fernando et al. |
| 2009/0260642 | A1 | 10/2009 | Monsees et al. |
| 2009/0272379 | A1 | 11/2009 | Thorens et al. |
| 2010/0031968 | A1 | 2/2010 | Sheikh et al. |
| 2010/0126505 | A1 | 5/2010 | Rinker |
| 2010/0181387 | A1 | 7/2010 | Zaffaroni et al. |
| 2010/0200008 | A1 | 8/2010 | Taieb |
| 2010/0242974 | A1 | 9/2010 | Pan |
| 2010/0307518 | A1 | 12/2010 | Wang |
| 2011/0005535 | A1 | 1/2011 | Xiu |
| 2011/0011396 | A1 | 1/2011 | Fang |
| 2011/0036346 | A1 | 2/2011 | Cohen et al. |
| 2012/0111347 | A1 | 5/2012 | Hon |

FOREIGN PATENT DOCUMENTS

| | | |
|---|---|---|
| CN | 1135860 | 11/1996 |
| CN | 1196660 A | 11/1996 |
| CN | 2293957 Y | 10/1998 |
| CN | 1252961 A | 5/2000 |
| CN | 1575673 A | 2/2005 |
| CN | 2719043 | 8/2005 |
| CN | 2719043 Y | 8/2005 |
| CN | 2719043 Y | 8/2005 |
| CN | 2777995 | 5/2006 |
| CN | 2777995 Y | 5/2006 |
| CN | 2870485 B | 2/2007 |
| CN | 200997909 Y | 1/2008 |
| CN | 101116542 A | 2/2008 |
| CN | 201018927 Y | 2/2008 |
| CN | 101176805 A | 5/2008 |
| CN | 201067079 Y | 6/2008 |
| CN | 201079011 Y | 7/2008 |
| CN | 201085044 Y | 7/2008 |
| CN | 201379072 Y | 1/2010 |
| CN | 201797997 U | 4/2011 |
| CN | 2887086 U | 11/2011 |
| CN | 202026802 U | 11/2011 |
| CN | 202026804 U | 11/2011 |
| DE | 10051792 A1 | 5/2002 |
| EP | 0057243 A1 | 8/1982 |
| EP | 0192950 A1 | 3/1986 |
| EP | 0230420 A1 | 8/1987 |
| EP | 0295122 A2 | 12/1988 |
| EP | 0342538 A2 | 11/1989 |
| EP | 0358002 A2 | 3/1990 |
| EP | 0295122 B1 | 1/1992 |
| EP | 0545186 A2 | 6/1993 |
| EP | 0703735 A1 | 4/1996 |
| EP | 0824927 A2 | 2/1998 |
| EP | 0845220 A1 | 6/1998 |
| EP | 0893071 A1 | 1/1999 |
| EP | 0951219 A1 | 10/1999 |
| GB | 1528391 A | 10/1978 |
| JP | 64000498 U | 1/1989 |
| JP | 06114105 A | 4/1994 |

(56) References Cited

FOREIGN PATENT DOCUMENTS

| | | |
|---|---|---|
| JP | 07506999 | 8/1995 |
| JP | 09075058 A | 3/1997 |
| UA | 47514 | 12/1997 |
| WO | WO-9409842 A1 | 5/1994 |
| WO | WO-9421317 A1 | 9/1994 |
| WO | WO-9740876 A2 | 11/1997 |
| WO | WO-9748293 A1 | 12/1997 |
| WO | WO-9817130 A1 | 4/1998 |
| WO | WO-0049901 A2 | 8/2000 |
| WO | WO0105459 A1 | 1/2001 |
| WO | WO-03034847 | 1/2003 |
| WO | WO-03022364 | 3/2003 |
| WO | WO-03055486 | 7/2003 |
| WO | WO-03101454 | 12/2003 |
| WO | WO-2004001407 | 12/2003 |
| WO | WO-2004023222 | 3/2004 |
| WO | WO-2004080216 | 9/2004 |
| WO | 2005099494 A | 10/2005 |
| WO | WO2005099494 A1 | 10/2005 |
| WO | WO-2006082571 | 8/2006 |
| WO | WO-2007078273 | 7/2007 |
| WO | WO-2008077271 | 7/2008 |
| WO | WO-2008130813 | 10/2008 |
| WO | WO-2009118085 | 10/2009 |
| WO | WO-2009135729 | 11/2009 |
| WO | WO-2010052323 | 5/2010 |
| WO | WO-2010145468 | 12/2010 |
| WO | WO-2010145805 | 12/2010 |
| WO | WO-2011010334 | 1/2011 |
| WO | WO-2011022431 | 2/2011 |

OTHER PUBLICATIONS

European Patent Office, Third Party Observation for EP Application No. 10740882, filed by Anonymous on Oct. 3, 2013.
IP Australia, Patent Examination Report No. 1 for AU 2010213240, Aug. 5, 2013.
Pan, Fenglin—Request for Invalidation of CN200920001296.3 in Chinese, along with English translation of same, Jun. 20, 2013.
State Intellectual Property Office, P.R. China, Office Action for CN201080016105.6, Aug. 30, 2013, with English translation.
State Intellectual Property Office, P.R. China, Decision of Patent Invalidation Petition, CN200720148285.9, Oct. 31, 2014 (Native and English Translation).
United States Patent and Trademark Office, Final Written Decision, CB Distributors, Inc. and DR Distributors, LLC v. Fontem Holdings 1 B. V., U.S. Pat. No. 8,156,944 B2, entered Dec. 24, 2014.
CN Creative and Intellicig USA, Ruyan v. Smoking Everywhere et al. CV11-6268 Invalidity Contentions, Apr. 12, 2012.
CN3111582.9, English Machine Translation corresponding to priority document of Hon '955.
CN200420031182, English Machine Translation corresponding to priority document of Hon '494.
Cyphert Gil DBA NU1S, Ruyan v. Smoking Everywhere et al. CV11-0367 Invalidity Contentions, Apr. 11, 2012.
European Patent Office, extended European Search Report for EP07721148, Dec. 6, 2010.
European Patent Office, extended European Search Report for EP11001479, Jul. 4, 2011.
European Patent Office, Supplemental Extended European Search Report for EP04718242, Jul. 27, 2007.
European Patent Office, Supplemental Partial Extended European Search Report for EP04718242, May 22, 2007.
European Patent Office, Supplementary Extended European Search Report for EP05729107, Jul. 31, 2007.
European Patent Office, Supplementary Partial Extended European Search Report for EP05729107, May 22, 2007.
FIN Branding Group, LLC, Request for Inter Partes Reexamination of U.S. Pat. No. 8,156,944, Sep. 13, 2012.
Introduction to selecting and using electronic components, ISBN7-111-13752-3.
IP Australia, Exam Report for AU2004234199, Aug. 14, 2009.
IP Australia, Examination Report for SG 200505930-8, May 4, 206.
IP Australia, Examination Report for SG200604498-6, Apr. 16, 2008.
IP Australia, Patent Examination Report No. 1 for AU2007250367, Jul. 30, 2012.
IP Australia, Patent Examination Report No. 1 for AU2007250368, Aug. 9, 2012.
Japanese Patent Office, Office Action for JP2006504199, Oct. 30, 2009.
Korean Intellectual Property Office, Ntc of Preliminary Rejection for KR1020057009767, Jul. 27, 2009.
Macau Patent Office, Official Communication for MOI121, Apr. 17, 2009.
Malaysian Patent Office, Examination Report for My PI 20041407, Sep. 28, 2007.
Manual for Electric Engineers, 2nd Ed, Mar. 2000.
Manual for Mechanical Designers, 4th Ed, Jan. 2002.
Materials Manual-Nonmetal, Jul. 1, 1985.
Sottera, Inc., Ruyan v. Smoking Everywhere et al. CV11-0367 Invalidity Contentions Exhibit 7 (Claim 20 Claim Chart), Apr. 12, 2012.
Sottera, Inc., Ruyan v. Smoking Everywhere et al. CV11-0367 Invalidity Contentions Exhibit 8 (Claim 24 Claim Chart), Apr. 12, 2012.
Sottera, Inc., Ruyan v. Smoking Everywhere et al. CV11-0367 Invalidity Contentions, Apr. 12, 2012.
State Intellectual Property Office, P.R. China, English translation of Written Opinion for PCT/CN07/001576, Aug. 3, 2007.
State Intellectual Property Office, P.R. China, International Search Report for PCT/CN04/000182, Jun. 10, 2004.
State Intellectual Property Office, P.R. China, International Search Report for PCT/CN05/000337, Jul. 14, 2005.
State Intellectual Property Office, P.R. China, English Translation of Written Opinion for PCT/CN07/001575, Jul. 20, 2007.
State Intellectual Property Office, P.R. China, International Search Report and Written Opinion for PCT/CN10/073613, Aug. 26, 2010.
State Intellectual Property Office, P.R. China, International Search Report for PCT/CN07/001575, Aug. 16, 2007.
State Intellectual Property Office, P.R. China, International Search Report for PCT/CN07/001576, Aug. 16, 2007.
State Intellectual Property Office, P.R. China, International Search Report for PCT/CN10/000125, Apr. 1, 2010.
State Intellectual Property Office, P.R. China, Search Report for Utility Model Patent ZL 200620090805.0, Nov. 18, 2008.
Taiwan Patent Office, Official Letter for TW093111573, Apr. 24, 2009.
TechPowerUp "What is a MOSFET, what does it look like and how does it work?" Dated May 24, 2004; 3 pgs. printed from Internet Jun. 4, 2011.
Ukraine Patent Office, Examination Report for UA200511258, Feb. 4, 2009.
United States Patent and Trademark Office, Office Action in Inter Partes Reexamination, mailed Nov. 27, 2012.
FIN Branding Group, LLC, Third Party Response to Amendment including Submission of Prior Arts and Misc. Statement Per 37 CFR 1.948 and Oljaca 6601776 in Reexamination of U.S. Pat. No. 8,156,944, Sep. 13, 2012.
Anonymous, Third Party Observations for EP20100740882, Apr. 11, 2014.
India Patent Office, First Examination Report for IN 8528/DELNP/2008, Mar. 27, 2014.
CB Distributors Inc. and DR Distributors, LLC , Petition for Inter Partes Review of U.S. Pat. No. 8,156,944 and Exhibits 1-20, filed Jun. 27, 2013.
Chen, Zhiyong—English Translation of Request for Invalidation of CN200620090805.0, Jun. 6, 2013.
Pan, Fenglin—Request for Invalidation of CN200720148285.9 in Chinese, along with English translation of same, filed Jun. 19, 2013.
United States Patent and Trademark Office, Non-final Office Action issued in U.S. Appl. No. 12/226,818 (Apr. 12, 2011).
United States Patent and Trademark Office, Non-final Office Action issued in U.S. Appl. No. 14/244,376 (Aug. 20, 2015).

(56) References Cited

OTHER PUBLICATIONS

U.S. District Court, Central District of California, Western Division, Defendant NJOY, Inc.'s Memorandum of Points and Authorities in Support of Defendants' Motion for Leave to Amend Invalidity Contentions Dated Jun. 29, 2015 and filed in Consolidated Case No. CV 14-01645 GW (MRW) and related consolidated cases.
U.S. District Court, Central District of California, Western Division, Defendant NJOY, Inc.'s Declaration of Brent K. Yamashita in Support of Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Exhibit 1 to Defendants' Motion for Leave to Amend Invalidity Contentions dated Jun. 29, 2015 and filed in Consolidated case No. CV 14-01645 GW (MRW) and related consolidated cases.
U.S. District Court, Central District of California, Western Division, Defendant NJOY, Inc.'s Exhibit 2 to Defendants' Motion for Leave to Amend Invalidity Contentions dated Jun. 29, 2015 and filed in Consolidated case No. CV 14-01645 GW (MRW) and related consolidated cases.
U.S. District Court, Central District of California, Western Division, Defendant NJOY, Inc.'s Exhibit 3 to Defendants' Motion for Leave to Amend Invalidity Contentions dated Jun. 29, 2015 and filed in Consolidated case No. CV 14-01645 GW (MRW) and related consolidated cases.
U.S. District Court, Central District of California, Western Division, Defendant NJOY, Inc.'s Exhibit 4 to Defendants' Motion for Leave to Amend Invalidity Contentions dated Jun. 29, 2015 and filed in Consolidated case No. CV 14-01645 GW (MRW) and related consolidated cases.
U.S. District Court, Central District of California, Western Division, Defendant NJOY, Inc.'s Exhibit 5 to Defendants' Motion for Leave to Amend Invalidity Contentions dated Jun. 29, 2015 and filed in Consolidated case No. CV 14-01645 GW (MRW) and related consolidated cases.
U.S. District Court, Central District of California, Western Division, Defendant NJOY, Inc.'s Reply Brief in Support of Defendants' Motion for Leave to Amend Invalidity Contentions dated Jul. 13, 2015 and filed in consolidated Case No. CV 14-01645 GW (MRW) and related consolidated cases.
U.S. District Court, Central District of California, Western Division, Defendant NJOY, Inc.'s production documents VLACHOS 0000061-72; Consolidated Case No. CV 14-01645 GW (MRW) and related consolidated cases.
European Patent Office, Observations by Third Parties in EP Patent Application No. 14173781.7 (Jan. 13, 2016).
Collins, John M., Expert Report—Invalidity (Excerpts), CV14-01645, Jun. 18, 2015.
Collins, John M., Expert Report—Invalidity CV14-01645-Appendix E-'742, Jun. 18, 2015.
Eisenfuhr Speiser PartGMBB, Notice and Grounds of Opposition to European Patent No. EP2022349, Apr. 30, 2015.
European Patent Office, extended European Search Report for EP14155503.7, Feb. 3, 2015.
European Patent Office, Partial European search report for EP14155503.7, Sep. 1, 2014.
Insmoke AG, Notice and Grounds of Opposition to European Patent No. EP202234942122, Apr. 28, 2015.
Intellectual Property Office of New Zealand, Exam Report for NZ572309, Apr. 21, 2010.
Israel Intellectual Property Office, Office Action for IL194768, Nov. 12, 2014.
Joyetech Deutschland GMBH, Notice and Grounds of Opposition against European Patent No. EP2022349, Mar. 10, 2015.
JT International S.A.. Petition for Inter Partes Review of U.S. Pat. No. 8,365,742—IPR2015-01587, Paper 1, Jul. 14, 2015.
JT International S.A., Petition for inter Partes Review of U.S. Pat. No. 8,365,742—IPR2015-01587, Ex. 1001, U.S. Pat. No. 8,365,742 ("'742 patent"), Jul. 14, 2015.
JT International S.A., Petition for Inter Partes Review of U.S. Pat. No. 8,365,742—IPR2015-01587, Ex. 1002, Declaration of Jeffrey A. Schuster, Ph.D., Jul. 14, 2015.
JT International S.A., Petition for Inter Partes Review of U.S. Pat. No. 8,365,742—IPR2015-01587, Ex. 1003, U.S. Pat. No. 6,155,268 ("Takeuchi"), Jul. 14, 2015.
JT International S.A., Petition for Inter Partes Review of U.S. Pat. No. 8,365,742—IPR2015-01587, Ex. 1004, U.S. Pat. No. 6,234,167 ("Cox"), Jul. 14, 2015.
JT International S.A., Petition for Inter Partes Review of U.S. Pat. No. 8,365,742—IPR2015-01587, Ex. 1005, U.S. Pat. No. 4,947,874 ("Brooks"), Jul. 14, 2015.
JT International S.A., Petition for Inter Partes Review of U.S. Pat. No. 8,365,742—IPR2015-01587, Ex. 1006, U.S. Pat. No. 2,057,353 ("Whittemore"), Jul. 14, 2015.
JT International S.A., Petition for Inter Partes Review of U.S. Pat. No. 8,365,742—IPR2015-01587, Ex. 1007, EP 0 845 220 ("Susa"), Jul. 14, 2015.
JT International S.A., Petition for Inter Partes Review of U.S. Pat. No. 8,365,742—IPR2015-01587, Ex. 1008, WO 2007/078273 A1 ("Liu"), Jul. 14, 2015.
JT International S.A., Petition for Inter Partes Review of U.S. Pat. No. 8,365,742—IPR2015-01587, Ex. 1009, '742 Prosecution History, Preliminary Amendment, Jul. 14, 2015.
JT International S.A., Petition for Inter Partes Review of U.S. Pat. No. 8,365,742—IPR2015-01587, Ex. 1010, '742 Prosecution History, Non-final Office Action, Jul. 14, 2015.
JT International S.A., Petition for Inter Partes Review of U.S. Pat. No. 8,365,742—IPR2015-01587, Ex. 1011, '742 Prosecution History, Amendment, Jul. 14, 2015.
JT International S.A., Petition for Inter Partes Review of U.S. Pat. No. 8,365,742—IPR2015-01587, Ex. 1012, '742 Prosecution History, Supplemental Amendment, Jul. 14, 2015.
JT International S.A., Petition for Inter Partes Review of U.S. Pat. No. 8,365,742—IPR2015-01587, Ex. 1013, '742 Prosecution History, Examiner Interview Summary, Jul. 14, 2015.
JT International S.A., Petition for Inter Partes Review of U.S. Pat. No. 8,365,742—IPR2015-01587, Ex. 1014, '742 Prosecution History, Notice of Allowance , Jul. 14, 2015.
JT International S.A., Petition for Inter Partes Review of U.S. Pat. No. 8,365,742—IPR2015-01587, Ex. 1015, '742 Prosecution History, Certificate of Correction, Jul. 14, 2015.
JT International S.A., Petition for Inter Partes Review of U.S. Pat. No. 8,365,742—IPR2015-01587, Ex. 1016, Fontem Litigation Joint Claim Construction Chart, Jul. 14, 2015.
JT International S.A., Petition for Inter Partes Review of U.S. Pat. No. 8,365,742—IPR2015-01587, Ex. 1017, Claim Construction Rulings in CV 14-1645 , Jul. 14, 2015.
JT International S.A., Petition for Inter Partes Review of U.S. Pat. No. 8,365,742—IPR2015-01587, Ex. 1018, Webster's New World Collegiate Dictionary ("detach"), Jul. 14, 2015.
JT International S.A., Petition for Inter Partes Review of U.S. Pat. No. 8,365,742—IPR2015-01587, Ex. 1019, Oxford American Dictionary & Thesaurus ("frame") , Jul. 14, 2015.
JT International S.A., Petition for Inter Partes Review of U.S. Pat. No. 8,365,742—IPR2015-01587, Ex. 1020, McGraw-Hill Dictionary of Scientific and Technical Terms (5th ed. 1994) ("assembly") ("component") ("porous") , Jul. 14, 2015.
JT International S.A., Petition for Inter Partes Review of U.S. Pat. No. 8,365,742—IPR2015-01587, Ex. 1021, Academic Press Dictionary ("permeability") ("solid"), Jul. 14, 2015.
JT International S.A., Petition for Inter Partes Review of U.S. Pat. No. 8,365,742—IPR2015-01587, Ex. 1022, American Heritage Dictionary ("atomize") ("end") ("substantial"), Jul. 14, 2015.
JT International S.A., Petition for Inter Partes Review of U.S. Pat. No. 8,365,742—IPR2015-01587, Ex. 1023, Merriam-Webster.com ("aerosol") ("atomizer") ("permeable") ("porous"), Jul. 14, 2015.
JT International SA, Notice and Grounds of Opposition against European Patent No. EP20223494, Apr. 30, 2015.
Khan, Sirahuddin, son of Samsuddin Khan, Pre-grant opposition ("representation") against IN8528/DELNP/2008, Jun. 20, 2014.
Korean Intellectual Property Office, Office Action for KR10-2008-7026879, Jun. 9, 2011.

(56) References Cited

OTHER PUBLICATIONS

Mexican Institute of Industrial Property, Exam Report for MX/a/2008/013526, Jul. 15, 2011.
Nicoventures Holdings Limited, Notice and Grounds of Opposition to European Patent No. EP2022349, Apr. 30, 2015.
NJOY, Inc. et al, Defendants' Joint Invalidity Contentions, CV14-01645 etc., Aug. 7, 2014.
NJOY, Inc. et al., Defendants' Joint Invalidity Contentions, CV-14-01645 etc., Attachment A—Claim Charts for U.S. Pat. No. 8,365,742, Aug. 7, 2014.
Philip Morris Products S. A., Notice and Grounds of Opposition to European Patent No. EP2022349, Apr. 30, 2015.
Ten Motives Limited, Notice and Grounds of Oppos.tion to European Patent No. EP2022349, Apr. 27, 2015.
United States Patent and Trademark Office Before the Patent Trial and Appeal Board, Inter Partes Review Institution Decision in IPR2013-00387, Paper 7, Dec. 30, 2013.
United States Patent and Trademark Office Office Action of U.S. Appl. No. 12/226,818, dated Apr. 12, 2011, 9 pages.
United States Patent and Trademark Office Office Action in U.S. Appl. No. 13/079,937, Jul. 19, 2012.
United States Patent and Trademark Office, Non-Final Office Action for U.S. Appl. No. 14/244,376, Sep. 4, 2014.
United States Patent and Trademark Office, Final Office Action for U.S. Appl. No. 14/244,376, Apr. 29, 2015.
VMR Products LLC, Petition for Inter Partes Review of U.S. Pat. No. 8,365,742—IPR2015-00859, Mar. 10, 2015.
VMR Products LLC, Petition for Inter Partes Review of U.S. Pat. No. 8,365,742—IPR2015-00859, Ex. 1001, U.S. Pat. No. 8,265,742, Mar. 10, 2015.
VMR Products LLC, Petition for Inter Partes Review of U.S. Pat. No. 8,365,742—IPR2015-00859, Ex. 1002, Buckner Declaration, Mar. 10, 2015.
VMR Products LLC, Petition for Inter Partes Review of U.S. Pat. No. 8,365,742—IPR2015-00859, Ex. 1003, Buckner CV, Mar. 10, 2015.
VMR Products LLC, Petition for Inter Partes Review of U.S. Pat. No. 8,365,742—IPR2015-00859, Ex. 1004, CN2719043, Mar. 10, 2015.
VMR Products LLC, Petition for Inter Panics Review of U.S. Pat. No. 8,365,742—IPR2015-00859, Ex. 1005, CN2719043—Certified Translation, Mar. 10, 2015.
VMR Products LLC, Petition for Inter Partes Review of U.S. Pat. No. 8,365,742—IPR2015-00859, Ex. 1006, WO2005099494, Mar. 10, 2015.
VMR Products LLC, Petition for Inter Partes Review of U.S. Pat. No. 8,365,742—IPR2015-00859, Ex. 1007, WO2005099494—Certified Translation, Mar. 10, 2015.
VMR Products LLC, Petition for Inter Partes Review of U.S. Pat. No. 8,365,742—IPR2015-00859, Ex. 1008, CA2562581, Mar. 10, 2015.
VMR Products LLC, Petition for Inter Partes Review of U.S. Pat. No. 8,365,742—IPR2015-00859, Ex. 1009, US20070267031, Mar. 10, 2015.
VMR Products LLC, Petition for Inter Partes Review of U.S. Pat. No. 8,365,742—IPR2015-00859, Ex. 1010, EP0845220, Mar. 10, 2015.
VMR Products LLC, Petition for Inter Partes Review of U.S. Pat. No. 8,365,742—IPR2015-00859, Ex. 1011, 055144962, Mar. 10, 2015.
VMR Products LLC, Petition for Inter Partes Review of U.S. Pat. No. 8,365,742—IPR2015-00859, Ex. 1012, WO2003034847, Mar. 10, 2015.
VMR Products LLC, Petition for Inter Partes Review of U.S. Pat. No. 8,365,742—IPR2015-00859, Ex. 1013, 052057353, Mar. 10, 2015.
VMR Products LLC, Petition for Inter Partes Review of U.S. Pat. No. 8,365,742—IPR2015-00859, Ex. 1014, CV14-1645 Rulings on Claims (litigation proceedings), Mar. 10, 2015.
VMR Products LLC, Petition for Inter Partes Review of U.S. Pat. No. 8,365,742—IPR2015-00859, Ex. 1015, WO2007131449, Mar. 10, 2015.
VMR Products LLC, Petition for Inter Partes Review of U.S. Pat. No. 8,365,742—IPR2015-00859, Ex. 1016, 742 Prosecution History, Preliminary Amendment, Mar. 10, 2015.
VMR Products LLC, Petition for inter Partes Review of U.S. Pat. No. 8,365,742—IPR2015-00859, Ex. 1017, 742 Prosecution History, Non-final Office Action, Jul. 19, 2012, Mar. 10, 2015.
VMR Products LLC, Petition for Inter Partes Review of U.S. Pat. No. 8,365,742—IPR2015-00859, Ex. 1018, 742 Prosecution History, Amendment, Mar. 10, 2015.
VMR Products LLC, Petition for inter Partes Review of U.S. Pat. No. 8,365,742—IPR2015-00859, Ex. 1019, 742 Prosecution History, Supplemental Amendment, Mar. 10, 2015.
VMR Products LLC, Petition for Inter Partes Review of U.S. Pat. No. 8,365,742—IPR2015-00859, Ex. 1020, 742 Prosecution History, Examiner interview Summary, Mar. 10, 2015.
VMR Products LLC, Petition for inter Partes Review of U.S. Pat. No. 8,365,742—IPR2015-00859, Ex. 1021, 742 Prosecution History, Notice of Allowance, Mar. 10, 2015.
VMR Products LLC, Petition for Inter Partes Review of U.S. Pat. No. 8,365,742—IPR2015-00859, Ex. 1022, 742 Prosecution History, Certificate of Correction, Mar. 10, 2015.
VMR Products LLC, Petition for Inter Partes Review of U.S. Pat. No. 8,365,742—IPR2015-00859, Ex. 1023, Decision—Institution of Inter Partes Review in IPR2013-00387, Paper 7, Mar. 10, 2015.
Wikipedia Entry "Heating Element", Jul. 23, 2007 (D10 of Joyetech EP Opposition above).
Nu Mark LLC, Petition for Inter Partes Review of U.S. Pat. No. 8,365,742—IPR2016-01303, Paper 1, Jun. 28, 2016.
Nu Mark LLC, Petition for Inter Partes Review of U.S. Pat. No. 8,365,742—IPR2016-01303, Ex.1001 U.S. Pat. No. 8,365,742 ("the 742 Patent"), Jun. 28, 2016.
Nu Mark LLC, Petition for Inter Partes Review of U.S. Pat. No. 8,365,742—IPR2016-01303, Ex.1002 Excerpts of the prosecution history for U.S. Pat. No. 8,365,742, Jun. 28, 2016.
Nu Mark LLC, Petition for Inter Partes Review of U.S. Pat. No. 8,365,742—IPR2016-01303, Ex.1003 Declaration of John M. Collins, Ph.D. ("Collins Decl."), Jun. 28, 2016.
Nu Mark LLC, Petition for Inter Partes Review of U.S. Pat. No. 8,365,742—IPR2016-01303, Ex.1004 U.S. Pat. No. 6,155,268 ("Takeuchi"), Jun. 28, 2016.
Nu Mark LLC, Petition for Inter Partes Review of U.S. Pat. No. 8,365,742—IPR2016-01303, Ex.1005 U.S. Pat. No. 2,057,353 ("Whittemore"), Jun. 28, 2016.
Nu Mark LLC, Petition for Inter Partes Review of U.S. Pat. No. 8,365,742—IPR2016-01303, Ex.1006 U.S. Pat. No. 4,947,874 ("Brooks"), Jun. 28, 2016.
Nu Mark LLC, Petition for Inter Partes Review of U.S. Pat. No. 8,365,742—IPR2016-01303, Ex.1007 Docket entry #65 from *Fontem Ventures, B.V., et al.* v. *Njoy, Inc., et al.*, 2:14-cv-01645 (C.D. Cal.) ("Rulings on Claim Construction"), Jun. 28, 2016.
Nu Mark LLC, Petition for Inter Partes Review of U.S. Pat. No. 8,365,742—IPR2016-01303, Ex.1008 U.S. Patent Application No. 2006/0093977 A1 ("Pellizzari I"), Jun. 28, 2016.
Nu Mark LLC, Petition for Inter Partes Review of U.S. Pat. No. 8,365,742—IPR2016-01303, Ex.1009 U.S. Pat. No. 7,059,307 ("Pellizzari II"), Jun. 28, 2016.
Nu Mark LLC, Petition for Inter Partes Review of U.S. Pat. No. 8,365,742—IPR2016-01303, Ex.1010 U.S. Pat. No. 5,894,841 ("Voges"), Jun. 28, 2016.
Nu Mark LLC, Petition for Inter Partes Review of U.S. Pat. No. 8,365,742—IPR2016-01303, Ex.1011 U.S. Pat. No. 5,743,251 ("Howell"), Jun. 28, 2016.
Nu Mark LLC, Petition for Inter Partes Review of U.S. Pat. No. 8,365,742—IPR2016-01303, Ex.1012 U.S. Pat. No. 2,461,664 ("Smith"), Jun. 28, 2016.
Nu Mark LLC, Petition for Inter Partes Review of U.S. Pat. No. 8,365,742—IPR2016-01303, Ex.1013 U.S. Pat. No. 3,234,357 ("Eberhard"), Jun. 28, 2016.

(56) References Cited

OTHER PUBLICATIONS

Nu Mark LLC, Petition for Inter Partes Review of U.S. Pat. No. 8,365,742—IPR2016-01303, Ex.1014 U.S. Pat. No. 5,745,985 ("Ghosh"), Jun. 28, 2016.
Nu Mark LLC, Petition for Inter Partes Review of U.S. Pat. No. 8,365,742—IPR2016-01303, Ex.1015 U.S. Pat. No. 4,676,237 ("Wood"), Jun. 28, 2016.
Nu Mark LLC, Petition for Inter Partes Review of U.S. Pat. No. 8,365,742—IPR2016-01303, Ex.1016 U.S. Pat. No. 4,945,448 ("Bremenour"), Jun. 28, 2016.
Nu Mark LLC, Petition for Inter Partes Review of U.S. Pat. No. 8,365,742—IPR2016-01303, Ex.1017 U.S. Pat. No. 2,442,004 ("Hayward-Butt"), Jun. 28, 2016.
Nu Mark LLC, Petition for Inter Partes Review of U.S. Pat. No. 8,365,742—IPR2016-01303, Ex.1018 U.S. Pat. No. 3,200,819 ("Gilbert"), Jun. 28, 2016.
Nu Mark LLC, Petition for Inter Partes Review of U.S. Pat. No. 8,365,742—IPR2016-01303, Ex.1019 U.S. Pat. No. 6,501,052 ("Cox"), Jun. 28, 2016.
Nu Mark LLC, Petition for Inter Partes Review of U.S. Pat. No. 8,365,742—IPR2016-01303, Ex.1020 U.S. Pat. No. 6,491,233 ("Nichols"), Jun. 28, 2016.
R.J. Reynolds Vapor Company, Petition for Inter Partes Review of U.S. Pat. No. 8,365,742—IPR2016-01268, Paper 2, Jul. 2, 2016.
R.J. Reynolds Vapor Company, Petition for Inter Partes Review of U.S. Pat. No. 8,365,742—IPR2016-01268, Ex. 1001 U.S. Pat. No. 8,365,742 to Lik Hon, Jul. 2, 2016.
R.J. Reynolds Vapor Company, Petition for Inter Partes Review of U.S. Pat. No. 8,365,742—IPR2016-01268, Ex. 1002 Chinese Pat. No. 2719043Y to Lik Hon, Jul. 2, 2016.
R.J. Reynolds Vapor Company, Petition for Inter Partes Review of U.S. Pat. No. 8,365,742—IPR2016-01268, Ex. 1003 Certified English translation of Chinese Pat. No. 2719043Y to Lik Hon, Jul. 2, 2016.
R.J. Reynolds Vapor Company, Petition for Inter Partes Review of U.S. Pat. No. 8,365,742—IPR2016-01268, Ex. 1004 U.S. Pat. No. 2,057,353 to C. L. Whittemore, Jr, Jul. 2, 2016.
R.J. Reynolds Vapor Company, Petition for Inter Partes Review of U.S. Pat. No. 8,365,742—IPR2016-01268, Ex. 1005 Application Data Sheet of Apr. 5, 2011 Filed in U.S. Pat. Appl. No. 13/079,937, Jul. 2, 2016.
R.J. Reynolds Vapor Company, Petition for Inter Partes Review of U.S. Pat. No. 8,365,742—IPR2016-01268, Ex. 1006 Preliminary Amendment of Apr. 5, 2011 Filed in U.S. Pat. Appl. No. 13/079,937, Jul. 2, 2016.
R.J. Reynolds Vapor Company, Petition for Inter Partes Review of U.S. Pat. No. 8,365,742—IPR2016-01268, Ex. 1007 Non-Final Office Action of Jul. 19, 2012 in U.S. Pat. Appl. No. 13/079,937, Jul. 2, 2016.
R.J. Reynolds Vapor Company, Petition for Inter Partes Review of U.S. Pat. No. 8,365,742—IPR2016-01268, Ex. 1008 Amendment of Aug. 3, 2012 in U.S. Pat. Appl. No. 13/079,937, Jul. 2, 2016.
R.J. Reynolds Vapor Company, Petition for Inter Partes Review of U.S. Pat. No. 8,365,742—IPR2016-01268, Ex. 1009 PCT Pub. No. WO2007131449, Jul. 2, 2016.
R.J. Reynolds Vapor Company, Petition for Inter Partes Review of U.S. Pat. No. 8,365,742—IPR2016-01268, Ex. 1010 English translation of PCT Pub. No. WO2007131449, Jul. 2, 2016.
R.J. Reynolds Vapor Company, Petition for Inter Partes Review of U.S. Pat. No. 8,365,742—IPR2016-01268, Ex. 1011 Board's Decision Denying Institution in IPR2015-00859, Jul. 2, 2016.
R.J. Reynolds Vapor Company, Petition for Inter Partes Review of U.S. Pat. No. 8,365,742—IPR2016-01268, Ex. 1012 Patent Owner's Preliminary Response to Petition for Ipr of U.S. Pat. No. 8,365,742 in IPR2015-00859, Jul. 2, 2016.
R.J. Reynolds Vapor Company, Petition for Inter Partes Review of U.S. Pat. No. 8,365,742—IPR2016-01268, Ex. 1013 Petition for IPR of U.S. Pat. No. 8,365,742 in IPR2015- 00859, Jul. 2, 2016.
R.J. Reynolds Vapor Company, Petition for Inter Partes Review of U.S. Pat. No. 8,365,742—IPR2016-01268, Ex. 1014 Board's Order Dismissing Petition in IPR2015-01587, Jul. 2, 2016.
R.J. Reynolds Vapor Company, Petition for Inter Partes Review of U.S. Pat. No. 8,365,742—IPR2016-01268, Ex. 1015 Declaration of Dr. Robert Sturges, Jul. 2, 2016.
R.J. Reynolds Vapor Company, Petition for Inter Partes Review of U.S. Pat. No. 8,365,742—IPR2016-01268, Ex. 1016 Rohsenow, "Heat, Mass, and Momentum Transfer", Jul. 2, 2016.
R.J. Reynolds Vapor Company, Petition for Inter Partes Review of U.S. Pat. No. 8,365,742—IPR2016-01268, Ex. 1017 WO 2005/099494, which is the PCT application equivalent of CN2719043Y to Hon ("Hon '494"), Jul. 2, 2016.
R.J. Reynolds Vapor Company, Petition for Inter Partes Review of U.S. Pat. No. 8,365,742—IPR2016-01268, Ex. 1018 Certified English translation of WO 2005/099494 pursuant to 37 C.F.R. 42.63(b), Jul. 2, 2016.

ELECTRONIC CIGARETTE

CROSS-REFERENCE TO RELATED APPLICATIONS

This application is a continuation of U.S. patent application Ser. No. 13/079,937, filed Apr. 5, 2011 and now pending, which is a divisional of U.S. patent application Ser. No. 12/226,818, filed Oct. 29, 2008 and now issued as U.S. Pat. No. 8,156,944, which is a 371 national filing of International Application No. PCTCN2007/001575, filed May 15, 2007, which claims priority to Chinese Patent Application No. 200620090805.0, filed May 16, 2006. All these applications are incorporated herein by reference in their entirety.

BACKGROUND ART

Smoking causes serious respiratory system diseases and cancer, though it is hard to persuade the smokers to completely quit smoking.

Nicotine is the effective ingredient in cigarettes. Nicotine acts on the receptor of the central nervous system.

Nicotine is a micromolecular alkaloid, which is basically harmless to human bodies at a small dosage. Plus, its half life period is extremely short in blood. Tar is the major harmful substance in tobacco. Tobacco tar comprises several thousands of ingredients, dozens of which are carcinogenic substances.

To provide cigarette substitutes that contain nicotine but not harmful tar, many products have been used. These products are not as harmful as tar, but are absorbed very slowly. As a result, smokers can't be satisfied in full. In addition, the smokers are deprived of the "smoking" habit.

The electronic cigarettes currently available on the market may resolve the above-mentioned issue, though they are complicated in structure, they don't provide the ideal aerosol effects, and their atomizing efficiency is not high. Their cigarette bodies can be roughly divided into three sections, which have to be connected via plugging or thread coupling before use.

SUMMARY OF INVENTION

To overcome the above-mentioned disadvantages, an aerosol electronic cigarette includes a battery assembly, an atomizer assembly and a bottle assembly. The battery assembly connects with the atomizer assembly and both are located in a housing. The bottle assembly is located in one end of the housing and fits with the atomizer assembly.

The battery assembly may include the battery, an operating indicator, electronic circuit board, and airflow sensor, which are connected with the battery, and with the signal output of the airflow sensor connected to the electronic circuit board.

A component for liquid storage of the cigarette bottle assembly stores the nicotine liquid. Smokers can enjoy the feel of smoking, with no fire hazard since there is no need for igniting.

SPECIFIC MODE FOR CARRYING OUT THE INVENTION

Figure 1:
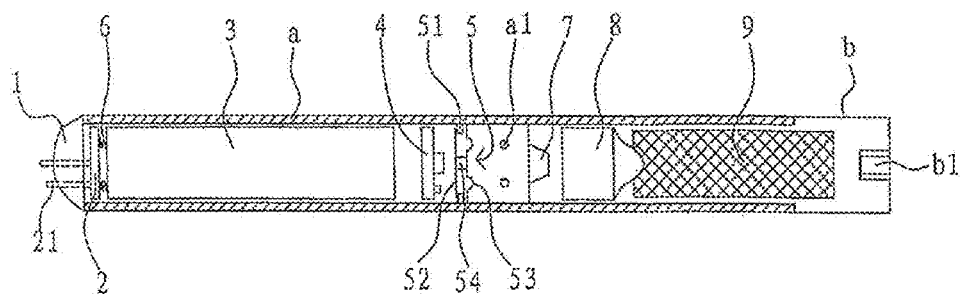
FIG. 1 is the side section view of an electronic cigarette.

As shown in FIGS. 1-10, an aerosol electronic cigarette includes a battery assembly, an atomizer assembly and a cigarette bottle assembly, and also includes a shell or housing (a), which is hollow and integrally formed. The battery assembly connects with the atomizer assembly and both are located in the shell. The cigarette bottle assembly is located in one end of the shell, which is detachable. The cigarette bottle assembly fits with the atomizer assembly. The shell has through-air-inlets (a1).

In this specific embodiment, the battery assembly includes the battery, and the operating indicator (1), electronic circuit board (4), and airflow sensor (5), which are connected with the battery. It also includes a check valve (7). The signal output of the airflow sensor (5) is connected with the said electronic circuit board (4). The battery is a rechargeable battery (3), which may be either a rechargeable polymer lithium ion battery or a rechargeable lithium ion battery. The airflow sensor (5) may be alternatively a semiconductor force-sensitive chip capacitance sensor or an inductance sensor.

The rechargeable battery (3) has a flexibly connected charging plug (2). The blades (21) of the charging plug (2) come out of the other end of the shell (a). Between the charging plug (2) and rechargeable battery (3) is a spring (6), which lies against the body of the rechargeable battery (3) on one end, while its free end lies against the charging plug (2), forming a flexible structure, which buffers the charging plug (2) when plugged for charging, thus protecting the rechargeable battery against any damage. Of course, the rechargeable battery (3) in this embodiment has a charging slot on it, which replaces the structure of charging plug (2) to perform the charging function and protect the rechargeable battery (3) against any damage. The operating indicator (1) is a LED. In this embodiment, there are two LEDs. The electronic circuit board (4) includes an electronic switch circuit, which controls the electric circuit according to the input signals, so that the rechargeable battery (3) electrifies the electric heating rod (82) inside the atomizer (8) and the LEDs as well.

Figure 2:
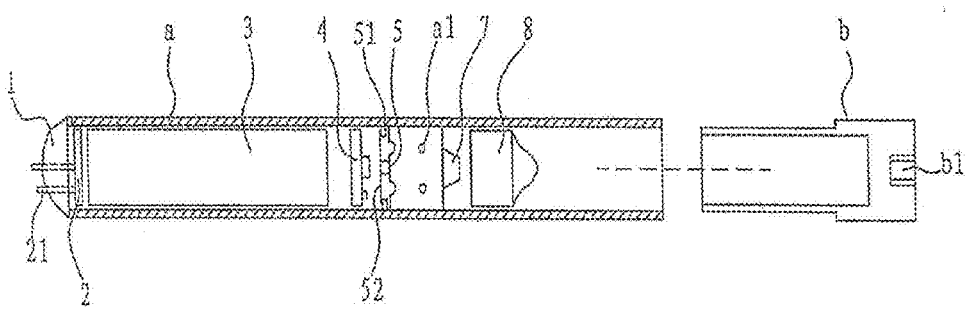
FIG. 2 is the section view of the housing (a) separated from the cigarette bottle assembly.

As shown in FIGS. 1 and 2, the airflow sensor (5) has a silica gel corrugated membrane (53), which connects with magnetic steel (54) with a reed relay (52) on one of its ends. Both ends of the said reed relay (52) correspond to the relay electrodes (51) respectively.

Figure 5:
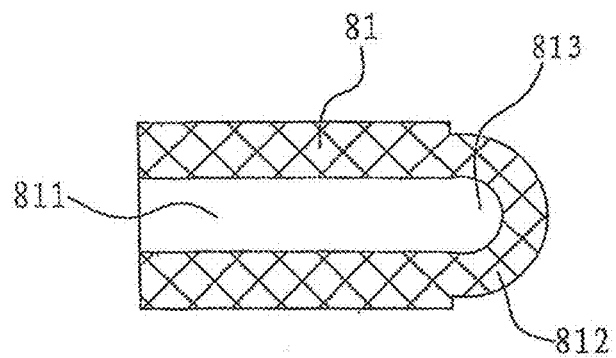
FIG. 5 is the side section view of a porous component of the atomizer.
Figure 6:
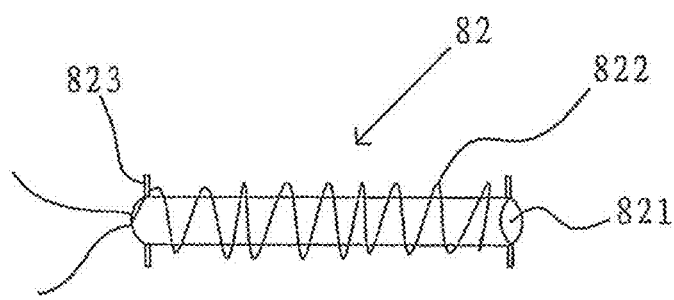
FIG. 6 is the diagram of the structure of an electric heating rod of the atomizer.
Figure 7:
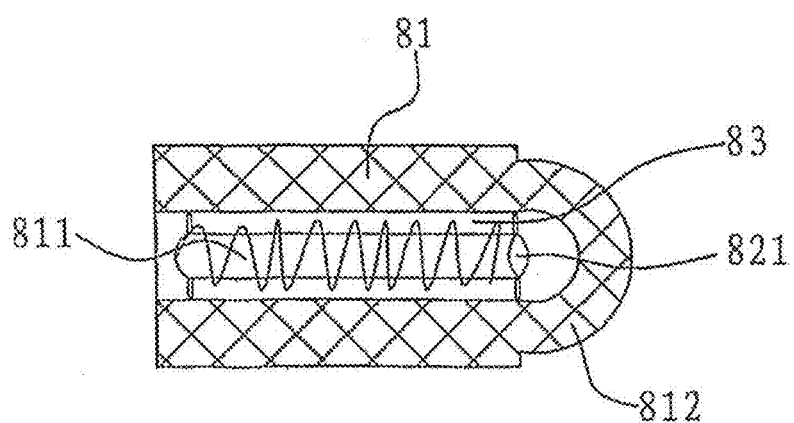
FIG. 7 is the side section of the atomizer, illustrating the locations of and connection relation between the electric heating rod and porous component.
Figure 8:
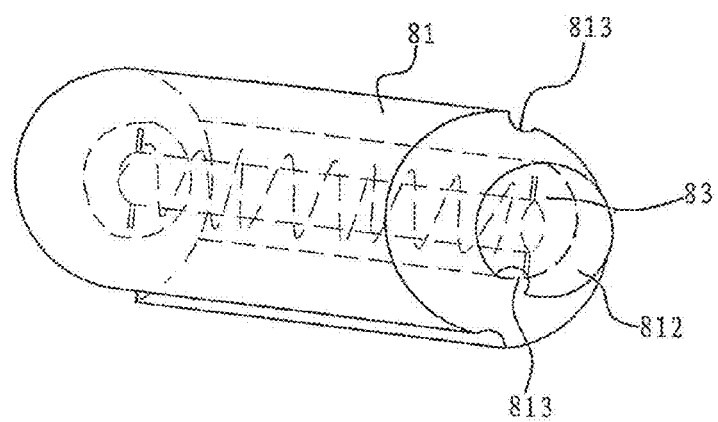
FIG. 8 is the diagram of the atomizer, illustrating the locations of and connection relation between the electric heating rod and porous component.
Figures 9, 10:
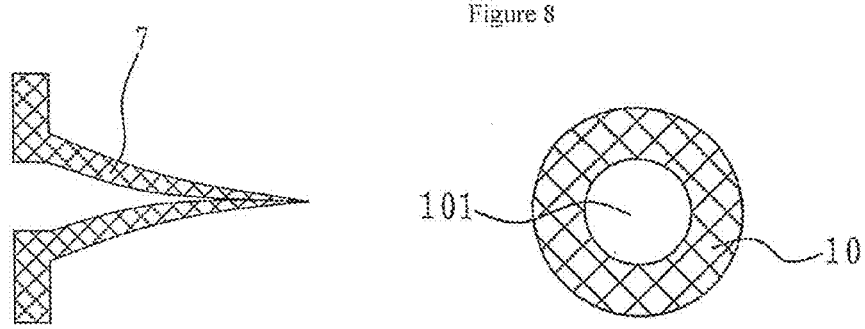
FIG. 9 is the section view of a check valve.
FIG. 10 is the front section view of a restriction component in a second embodiment.
Figures 11, 12:
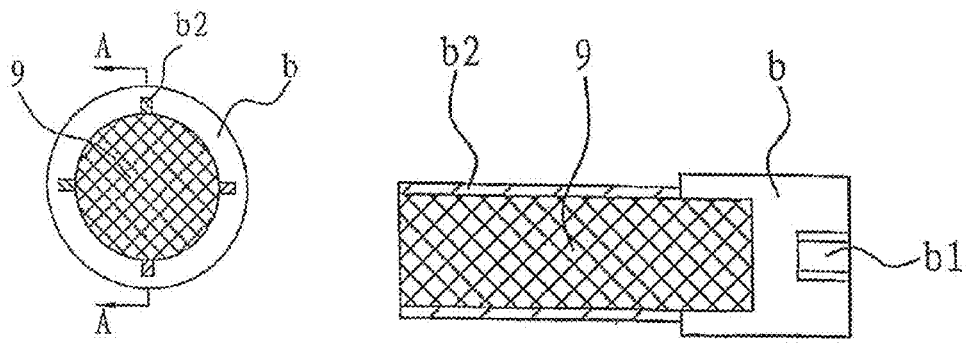
FIG. 11 is a diagram of the axial structure of the cigarette bottle assembly in another embodiment.
FIG. 12 is a sectional view taken along line A-A of FIG. 11.
Figure 13:
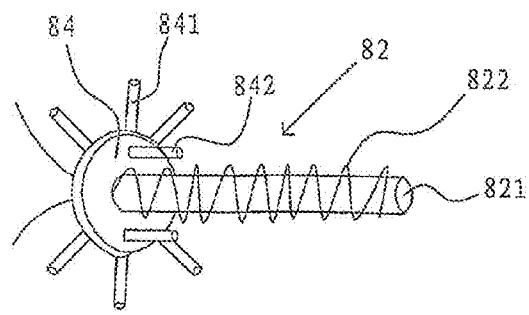
FIG. 13 is a diagram of the structure of the electric heating rod of the atomizer in another embodiment.
Figures 14, 15:
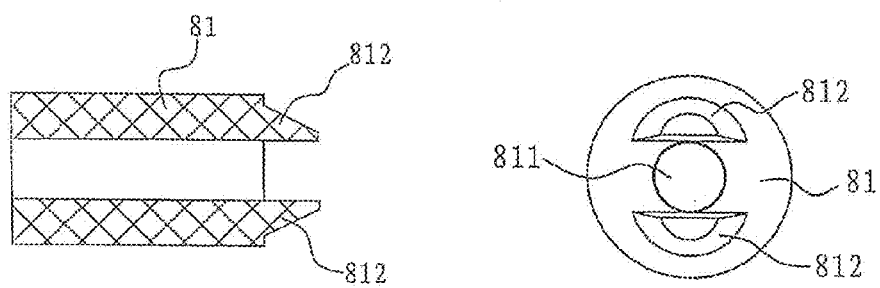
FIG. 14 is a section view of the porous component of the atomizer in the embodiment shown in FIG. 13.
FIG. 15 is a diagram of the axial structure of FIG. 14.
Figure 16:
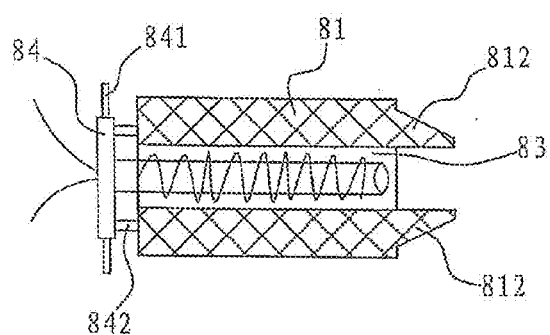
FIG. 16 is a side section view of the atomizer in the embodiment of FIG. 13, illustrating the locations of and connection relation between the electric heating rod and porous component.

As shown in FIGS. 5-8, the atomizer assembly is an atomizer (8), which includes a porous component (81) and a heating rod (82). The body of the porous component (82) has a run-through atomizing chamber (811). The diameter of the electric heating rod (82) is less than the diameter of the atomizing chamber (811). The electric heating rod (82) enters into the atomizing chamber (811), and there is a clearance between the electric heating rod (82) and interior wall of the atomizing chamber (811), which forms a negative pressure cavity (83). One end of the porous component (81) fits with the cigarette bottle assembly. As FIGS. 5, 7 and 8 show, the porous component (81) has a protuberance (812) on the other end, and the protuberance (812) fits with the cigarette bottle assembly. The protuberance (812) is a protruding half sphere, on the side of which there is a run-through hole (813) connecting to the atomizing chamber (811). Of course, the protuberance (812) may also be a taper, rectangle or any other shape. The porous component (81) is made of foamed nickel, stainless steel fiber felt, macromolecular polymer foam or foamed ceramics, providing the remarkable capabilities in liquid absorption and diffusion, and the ability to absorb the liquid stored in the cigarette bottle assembly.

As shown in FIG. 6, the electric heating rod (82) includes a cylinder (821). The heating wire (822) is wound on the wall of the cylinder (821). On the wall of both ends of the cylinder (821), there are mandrils (823) respectively, which lie against the interior wall of the atomizing chamber (811) of the porous component (81). There is a negative pressure cavity (83) between the electric heating rod and interior wall of the atomizing chamber.

The heating wire is made of platinum wire, nickel-chromium alloy wire or iron-chromium alloy wire containing rare earth, or is flaked. The electric heating rod (82) may alternatively have on its peripheral wall the heating layer made of electrically conductive ceramic PTC material, to replace the heating wire.

In this embodiment, the battery assembly and atomizer assembly are mutually connected and then installed inside the integrally formed shell (a) to form a one-piece part. The rechargeable battery (3) may be charged without frequent change of battery. The user just needs to plug the cigarette bottle assembly into the open end of the shell (a), for easy use and very easy change.

Figure 3:
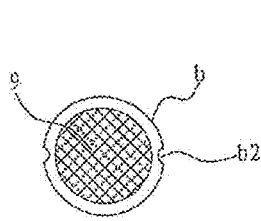
FIG. 3 is the diagram of the axial structure of the cigarette bottle assembly, illustrating the ventilating groove on the peripheral surface of the cigarette holder housing.
Figure 4:
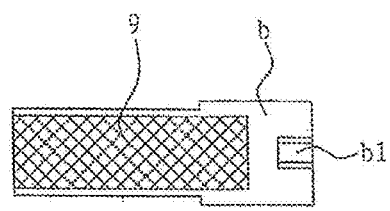
FIG. 4 is the side section view of the cigarette bottle assembly, illustrating the structure of the air channel.

As shown in FIGS. 3 and 4, the cigarette bottle assembly includes a hollow cigarette holder shell (b), and a perforated component for liquid storage (9) inside the shell (b). The perforated component for liquid storage (9) is made of such materials as PLA fiber, terylene fiber or nylon fiber, which are suitable for liquid storage. Alternatively, it may be plastic foam molding or column of multi-layer plates made through plastic injection with polyvinyl chloride, polypropylene and polycarbonate. One end of the cigarette holder shell (b) plugs into the shell (a), and the outer peripheral surface of the cigarette holder shell (b) has an inward ventilating groove (b2). On one end surface of the cigarette holder shell (b), there is an air channel (b1) extending inward. The air channel (b1) is located in the center on the surface of one end of shell (b).

As shown in FIGS. 1-9, one end of the porous component (81) lies against one end surface of the perforated component for liquid storage (9), and contacts the perforated component for liquid storage (9). It absorbs the cigarette liquid from the perforated component for liquid storage (9). When the smoker smokes, the cavity of the cigarette holder shell (b) is in the negative pressure state. In the shell (b), one end of the airflow sensor (5) forms a normal pressure cavity, while the other end forms a negative pressure cavity. The air pressure difference between the normal pressure cavity and negative pressure cavity or the high-speed airflow enables the magnetic steel (54) of the airflow sensor (5) to drive the reed relay (52) to contact the relay electrode (51).

Figure 20:
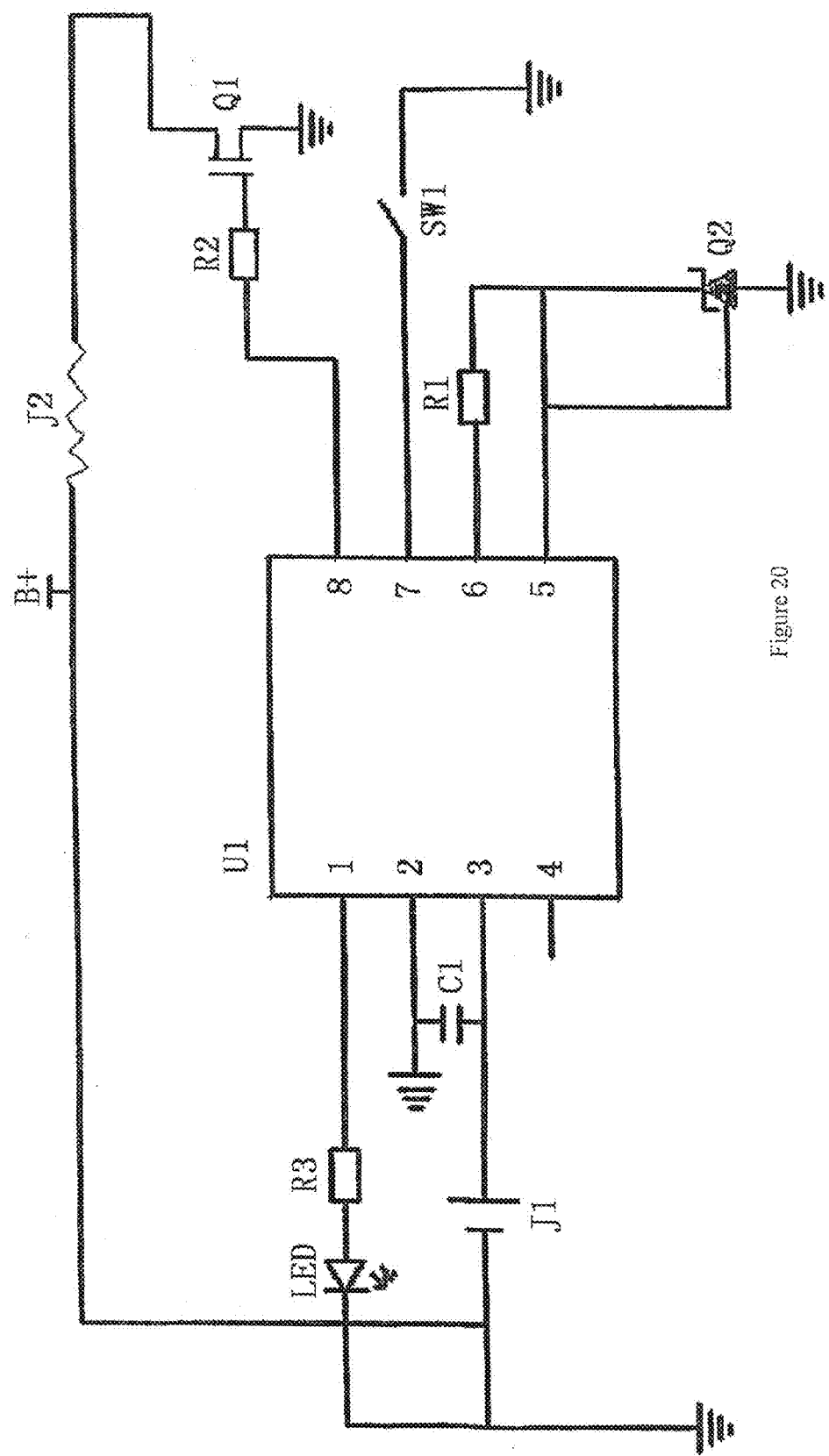
FIG. 20 is the electric circuit diagram of an electronic cigarette.

As shown in FIG. 20, the electric circuit is electrified, and the electronic switch circuit on the electronic circuit board (4) is electrified. Thus, the rechargeable battery (3) starts to electrify the electric heating rod (82) inside the atomizer (8), and at the same time, the LEDs, which are electrified by the rechargeable battery (3), emit light. The air enters the normal pressure cavity through the air inlet (a1), passes the check valve (7) via the airflow passage in the airflow sensor (5), and flows to the negative pressure cavity (83) in the atomizer (8). Since the negative pressure cavity (83) provides the negative pressure compared with the outside, the air flow sprays into it, bringing the cigarette liquid from the porous component (81) to spray into the negative pressure cavity (83) in the form of fine drops.

In the meantime, the electric heating rod (82) is electrified by the rechargeable battery (3) under the control of electronic circuit board (4), to heat the fine drops for atomization. After atomization, the big-diameter fine drops are re-absorbed by the porous component (81) under the action of vortex, while the small-diameter fine drips are suspended in the airflow to form aerosol, which is discharged through the negative pressure cavity (83) and run-through hole (813), flows into the cigarette holder shell (b) of the cigarette bottle assembly, and is absorbed by the air channel (b1). When the aerosol enters the cigarette holder shell (b), multiple small liquid drops are condensed into bigger ones, which fall into the clearance between the cigarette holder shell (b) and air channel (b1) without being absorbed by the air channel (b1). The perforated component for liquid storage (9) of the cigarette bottle assembly and the porous component (81) of the atomizer (8) contact each other to achieve the capillary impregnation for liquid supply.

The unit and its connecting structure of this invention may also be loaded with drugs for delivery to the lung.

Figure 22:
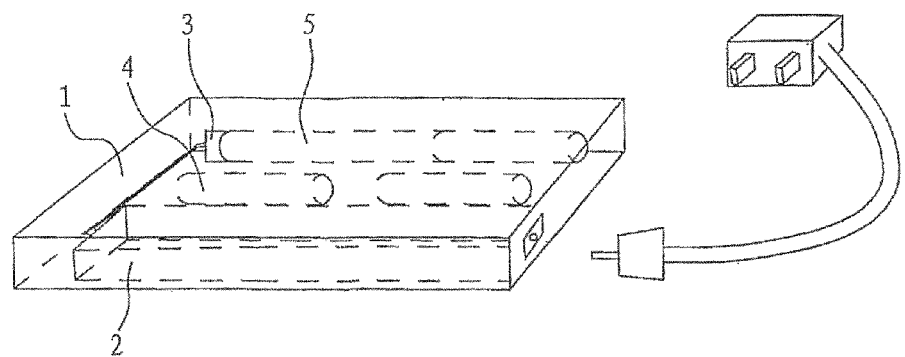
FIG. 22 is a diagram of a charging device, illustrating the locations of and connection relation of various internal parts.
Figure 23:
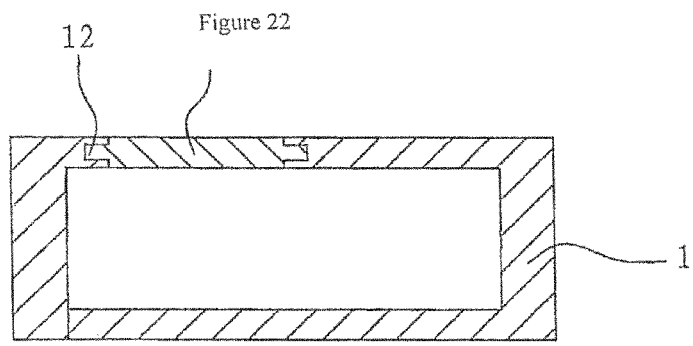
FIG. 23 is the side section view of the charging device.
Figure 24:
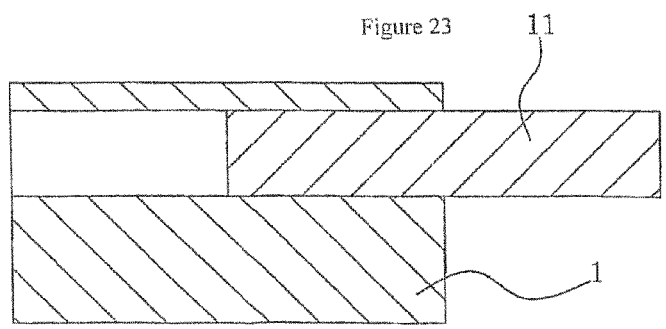
FIG. 24 is the diagram of the front structure of the charging device.

As shown in FIGS. 22, 23 and 24, the electronic cigarette (5) is held in a charging device. The charging device includes a case (1), which contains an auxiliary charging storage battery (2) inside it, and holds the electronic cigarette (5) and the charger (3) for the rechargeable battery embedded in the electronic cigarette (5), as well as the power supply circuit. The power inputs of the auxiliary charging storage battery (2) and charger (3) are connected with the power supply respectively. The charger (3) in this embodiment is a constant voltage & current charger. It may be a GY5210 charger, or any other constant voltage & current charger. The case (1) has a spare liquid supply bottle (4) in it. The power output of the auxiliary charging storage battery (2) is connected with the power input of the charger (3). The power output of the charger (3) is a charging slot (31), which fits with the charging plug of the rechargeable battery inside the electronic cigarette, or a charging plug, which fits with the charging slot of the rechargeable battery.

As shown in FIGS. 23 and 24, on the body of the shell (1), there is a pair of slide ways (12) corresponding to the position of the electronic cigarette, and on the slide ways, there is a slide cover (11).

In the second preferred embodiment, a restriction component (10), which is detachable, is set on one end of the porous component (81). There is a restriction hole (101) on the body of the restriction component (10). The restriction hole (101) corresponds to the atomizing chamber (811). The pore diameter of the restriction hole is less than the inner diameter of the atomizing chamber (811) to the extent that the size of the restriction component (10) installed on the porous component (81) varies, for the purpose of airflow capacity control. On the basis of different applications, the restriction component of different sizes and pore diameters may be used.

In the third preferred embodiment of this utility model, as shown in 11 and 12, on the outer peripheral wall of the cigarette shell (b), there is a protruding rib (b2) that is evenly partitioned. The perforated component for liquid storage (9) enters the cigarette holder shell (b) and lies against the protruding rib (b2). Thus, there appears a clearance between the outer peripheral surface of the perforated component for liquid storage (9) and the interior wall of the shell (b). The clearance is for connection the shell (a) and cigarette holder shell (b). When the user smokes, the air channel (b1) absorbs the air to cause airflow inside the shell (a), thus triggering the airflow sensor (5) and eventually starting the electronic cigarette. Also, the atomizer (8) works to atomize the cigarette liquid and produce gas flow, which enters the cigarette holder shell (b).

In the fourth preferred embodiment, as shown in FIGS. 13, 14, 15 and 16, on one end of the cylinder (821), there is a fixed plate (84), whose outer peripheral wall has partitioned supports (841). The outer ends of the supports (841) lie against the interior wall of the shell (a), thus suspending the cylinder (821), which is connected with the fixed plate (84), in the cavity of the shell (a). On the surface of the fixed plate (84), there is a mandril (842), whose front end lies against one end of the porous component (81), so that the fixed plate (84) is separated from the atomizing chamber (811) of the porous component (81). As a result, the run-through hole on one end of the atomizing chamber (811) won't be blocked, and the mist generated in the atomizing chamber (811) can be dispersed. One end of the porous component (81) has two protuberances (812) at the outlet of the atomizing chamber (811). Between the two protuberances (812) is a clearance. The two protuberances (812) lie against the perforated component for liquid storage (9).

Figure 17:
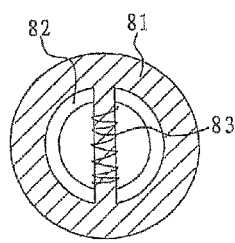
FIG. 17 is a diagram of the axial structure of the atomizer in another embodiment.
Figure 18:
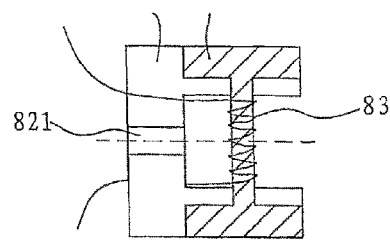
FIG. 18 is the side section view of the atomizer shown in FIG. 17.

In the fifth preferred embodiment, as shown in FIGS. 17 and 18, the atomizer assembly is an atomizer (8), which includes a frame (82), the porous component (81) set on the frame (82), and the heating wire (83) wound on the porous component (81). The frame (82) has a run-through hole (821) on it. The porous component (81) is wound with heating wire (83) in the part that is on the side in the axial direction of the run-through hole (821). One end of the porous component (81) fits with the cigarette bottle assembly. The porous component (81) is made of foamed nickel, stainless steel fiber felt, macromolecular polymer foam or foamed ceramics.

Figure 19:
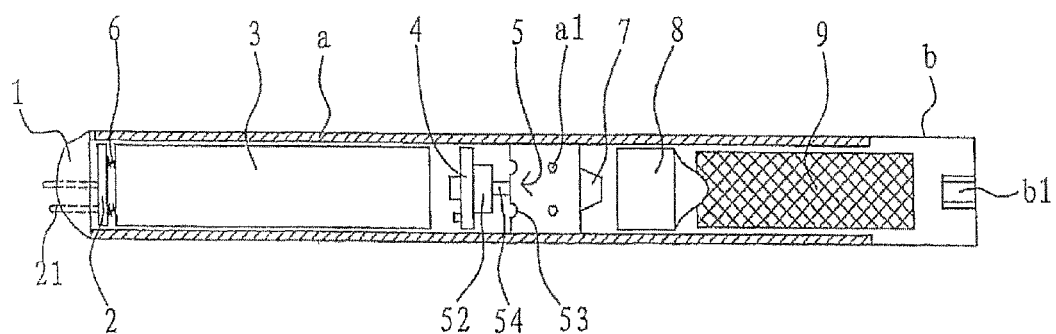
FIG. 19 is the side section view of another electronic cigarette embodiment.
Figure 21:
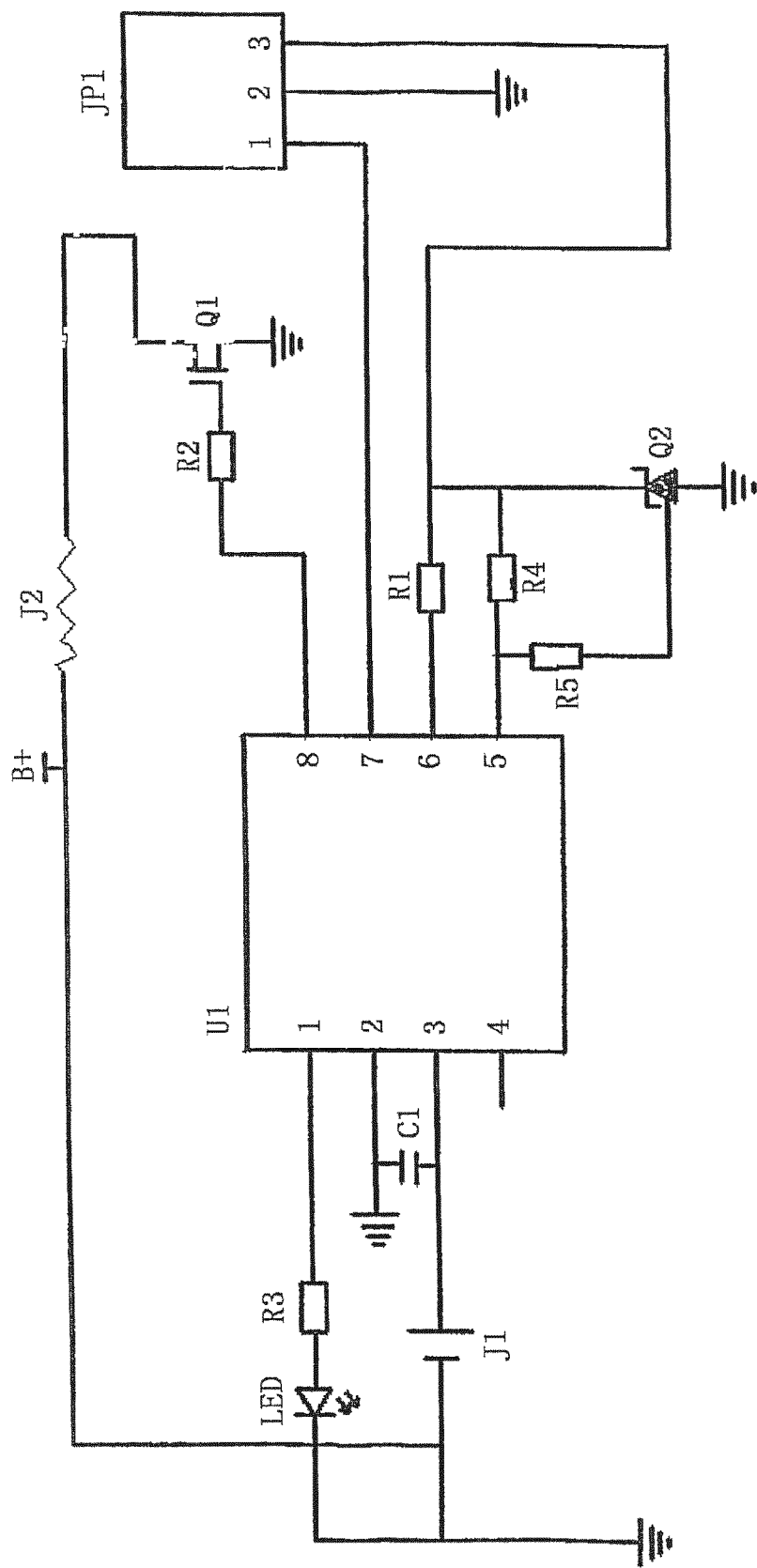
FIG. 21 is another electric circuit diagram of an electronic cigarette.

In the sixth preferred embodiment, as shown in FIG. 19, the airflow sensor (5) has a silica gel corrugated membrane (53), which connects with magnetic steel (54) with a Hall element (52), or a magneto-diode or a magneto-triode on one of its ends. FIG. 21 shows the electric circuit of the electronic cigarette of this solution.

The invention claimed is:

1. A electronic vaporizing device, comprising:
  a battery and a liquid storage component in an elongated cylindrical housing having at least one air inlet and an outlet;
  a hollow cylindrical component comprising a fiber material, with the hollow cylindrical component in the elongated cylindrical housing and having a central axis parallel to a longitudinal axis of the elongated cylindrical housing, with the hollow cylindrical component in contact with the liquid storage component, and an atomizing chamber formed within inner cylindrical walls of the hollow cylindrical component between a front end opening and a back end opening of the hollow cylindrical component, to allow air to flow into the atomizing chamber from the front end opening and out from the back end opening of the hollow cylindrical component;
  an air flow path from the one or more air inlets through the atomizing chamber in the hollow cylindrical component, to the outlet; and
  a wire coil in the atomizing chamber wound on a porous component and electrically connected to the battery.

2. The device of claim 1 further including a restriction component in the air flow path having a restriction hole concentric with the front end opening of the hollow cylindrical component.

3. The device of claim 1 further including a plate fixed in place in the elongated cylindrical housing at the front end opening of the hollow cylindrical component, with the plate in contact with the hollow cylindrical component.

4. The device of claim 3 with the wire coil having first and second wire leads passing out of the front end opening of the hollow cylindrical component, and with the first and second wire leads extending through the plate, for connecting the wire coil to the battery.

5. The device of claim 3 with the atomizing chamber having a uniform diameter along the length of the atomizing chamber, and the plate having a diameter larger than the diameter of the atomizing chamber.

6. The device of claim 1 with the front end opening and the back end opening of the hollow cylindrical component having equal diameters.

7. The device of claim 1 with the hollow cylindrical component having a single front end opening.

8. The device of claim 1 with the liquid storage component at a position in the elongated cylindrical housing between the outlet and the hollow cylindrical component.

9. The device of claim 1 further including a restriction component between the hollow cylindrical component and the at least one inlet, with the restriction component having a restriction hole smaller than the front end opening of the hollow cylindrical component.

10. The device of claim 1 with the hollow cylindrical component having an outer cylindrical sidewall having a first diameter, and with the wire coil having an outer diameter less than the first diameter.

11. The device of claim 10 with the atomizing chamber parallel to the longitudinal axis.

12. The device of claim 11 with the wire coil including first and second wire leads passing out of the front end opening of the porous component.

13. The device of claim 12 further comprising a frame including a first section having a first diameter and a second section having a second diameter less than the first diameter, and with second section inserted into the front end opening of the hollow cylindrical component.

14. A vaporizing device, comprising:
a battery assembly and an atomizer assembly within an elongated cylindrical housing with the battery assembly electrically connected to the atomizer assembly;
a liquid storage component in the elongated cylindrical housing;
with the elongated cylindrical housing having one or more air inlets;
the atomizer assembly including an atomization chamber having a front end opening and a back end opening to allow air to flow into the atomization chamber from the front end opening and out from the back end opening; and
a heating wire coil wound on a porous component that is perpendicular to a longitudinal axis of the elongated cylindrical housing, with the heating wire coil in an air flow path between the front end opening and the back end opening of the atomization chamber.

15. The device of claim 14 with the atomization chamber having a uniform diameter along the length of the atomization chamber.

16. The device of claim 14 with the heating wire coil having an outer diameter less than an inner diameter of the atomizing chamber.

17. The device of claim 14 further comprising a check valve between the inlet and the porous component.

18. The device of claim 14 further including a restriction component between the hollow cylindrical component and the at least one air inlet, with the restriction component having a restriction hole smaller than the open front end of the hollow cylindrical component.

19. The device of claim 14 further including a plate fixed in place in the tubular housing, with the plate in contact with the front end of the hollow cylindrical component, and the atomization chamber having a uniform diameter along the length of the atomization chamber, and the plate having a diameter larger than the uniform diameter of the atomization chamber.

* * * * *